(12) United States Patent
Talbot et al.

(10) Patent No.: US 8,550,997 B2
(45) Date of Patent: Oct. 8, 2013

(54) SENSOR AND MONITOR SYSTEM

(75) Inventors: Cary Talbot, Santa Clarita, CA (US);
Kris R. Holtzclaw, Santa Clarita, CA (US); Hans K. Wenstad, Santa Clarita, CA (US); Gary Cohen, Sherman Oaks, CA (US); Brian T. Kannard, Los Angeles, CA (US); Keith E. DeBrunner, Simi Valley, CA (US); Joseph Makram Arsanious, Riverside, CA (US); Fan Meng, San Marino, CA (US); Andrew Michael Bryan, Los Angeles, CA (US); Ulrich H. Rankers, Livermore, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 572 days.

(21) Appl. No.: 12/651,213

(22) Filed: Dec. 31, 2009

(65) Prior Publication Data
US 2011/0160553 A1    Jun. 30, 2011

(51) Int. Cl.
*A61B 5/00* (2006.01)
*A61B 5/05* (2006.01)

(52) U.S. Cl.
USPC .......................... 600/365; 600/316; 600/347

(58) Field of Classification Search
USPC ........................................ 600/316, 347, 365
See application file for complete search history.

(56) References Cited

U.S. PATENT DOCUMENTS

| | | | | |
|---|---|---|---|---|
| 5,606,978 | A * | 3/1997 | Armstrong et al. | 600/524 |
| 6,424,847 | B1 * | 7/2002 | Mastrototaro et al. | 600/316 |
| 7,392,077 | B2 * | 6/2008 | Mueller et al. | 600/427 |
| 2007/0056584 | A1 * | 3/2007 | Jagger et al. | 128/201.21 |
| 2007/0173712 | A1 * | 7/2007 | Shah et al. | 600/347 |
| 2008/0114229 | A1 * | 5/2008 | Brown | 600/365 |
| 2008/0269585 | A1 * | 10/2008 | Ginsberg | 600/365 |
| 2010/0025238 | A1 * | 2/2010 | Gottlieb et al. | 204/401 |
| 2010/0331652 | A1 * | 12/2010 | Groll et al. | 600/365 |

OTHER PUBLICATIONS

Meaney, Scott. "New 16GB Lexar JumpDrive Secure II Plus USB Flash Drive Doubles Memory Capacity of Popular Storage Device." Lexar Press Release. Aug. 25, 2008.*

* cited by examiner

*Primary Examiner* — Michael Kahelin
*Assistant Examiner* — Yunqing Wang
(74) *Attorney, Agent, or Firm* — Medtronic MiniMed, Inc.

(57) ABSTRACT

A monitor system is disclosed. The monitor system includes a sensor with a sensor port. The monitor system further includes a recorder with a recorder port within a recording housing. The recorder port interfaces with the sensor port to receive signals from the sensor port. A recorder clock is defined within the recorder housing, with a recorder processor to store signals from the sensor. The recorder includes a data port to interface with a dock receiver. The monitor system includes a dock remotely located from the sensor and the recorder. The dock receiver couples the recorder to the dock. The monitor system further includes a data processor to analyze the sensor signals from the recorder. The data processor includes memory and a clock. Further included with the data processor are program instructions to assign the time and date of the sensor signals.

19 Claims, 10 Drawing Sheets

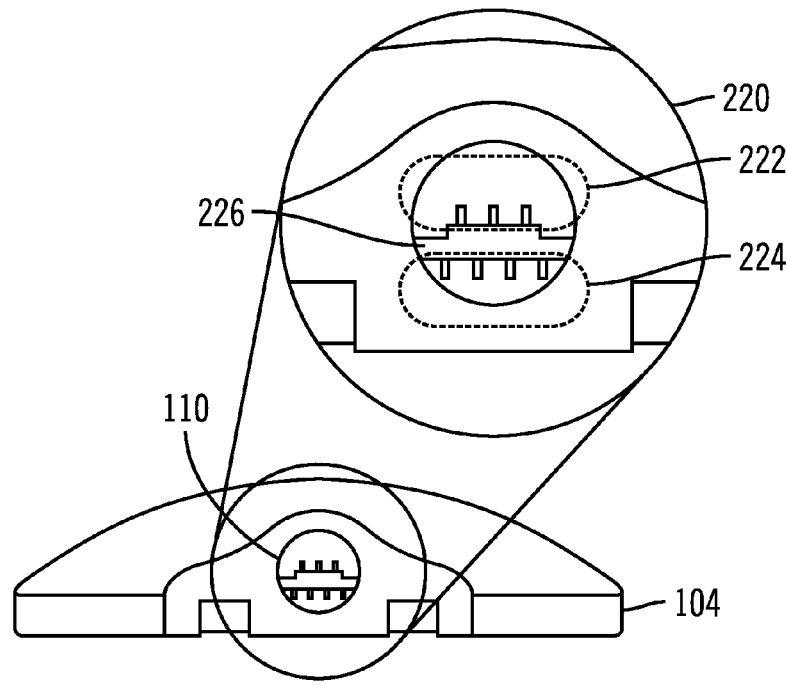
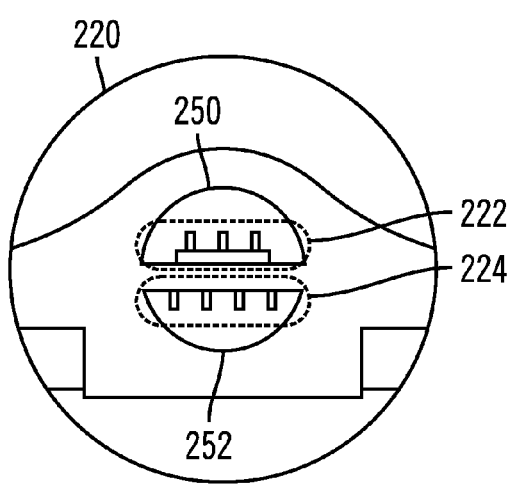 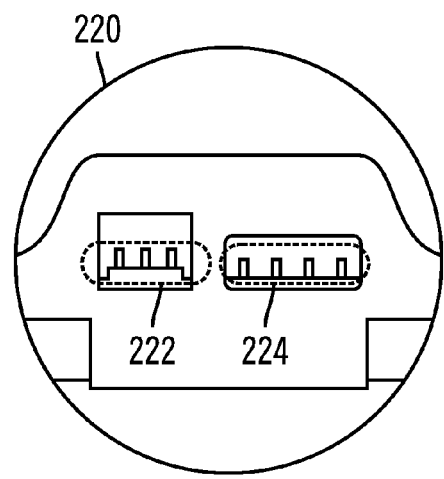
FIG. 2B
FIG. 2C
FIG. 2D

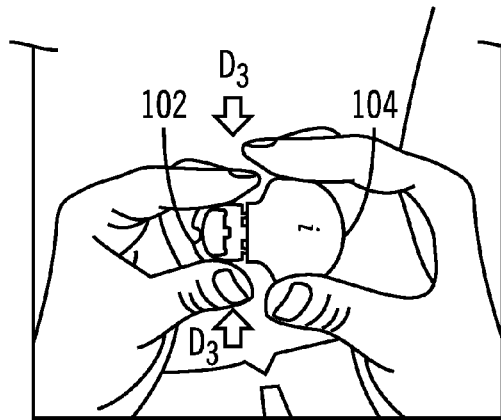
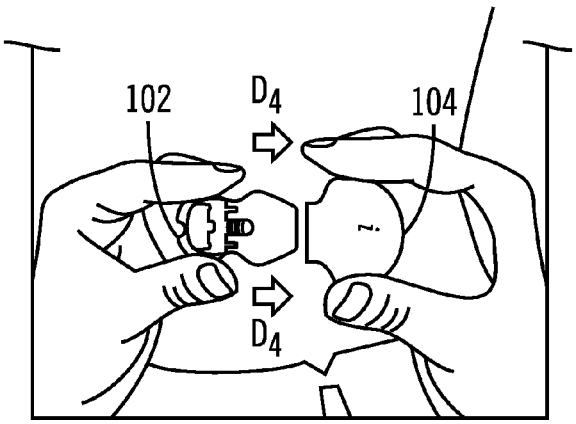
FIG. 6A  FIG. 6B
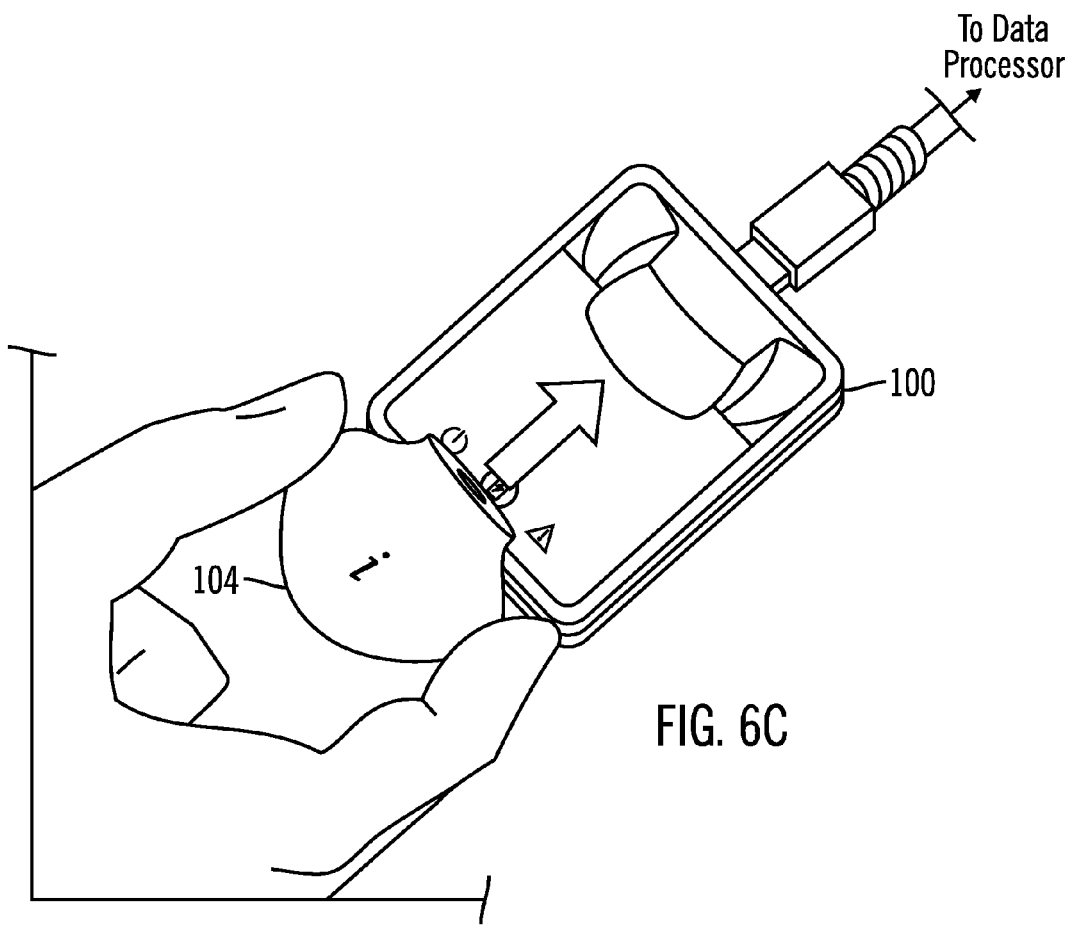
FIG. 6C

SENSOR AND MONITOR SYSTEM

FIELD OF THE INVENTION

This invention relates to monitor systems and, in particular embodiments, to devices and methods for monitoring of an sensor to determine a characteristic of a body.

BACKGROUND OF THE INVENTION

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein, also see U.S. Pat. No. 5,299,571. However, the monitors for these continuous sensors provide alarms, updates, trend information and require sophisticated hardware to allow the user to program the monitor, calibrate the sensor, enter data and view data in the monitor and to provide real-time feedback to the user. This sophisticated hardware makes it most practical for users that require continuous monitoring with feedback to maintain tight control over their conditions. In addition, these systems require the user to be trained in their use, even if to be worn for short periods of time to collect medical data which will be analyzed later by a doctor.

Doctors often need continuous measurements of a body parameter over a period of time to make an accurate diagnosis of a condition. For instance, Holter monitor systems are used to measure the EKG of a patient's heart over a period of time to detect abnormalities in the heart beat of the patient. Abnormalities detected in this manner may detect heart disease that would otherwise go undetected. These tests, while very useful are limited to monitoring of bio-mechanical physical changes in the body, such as a heart beat, respiration rate, blood pressure or the like.

SUMMARY OF THE DISCLOSURE

A monitor system to monitor a characteristic of a user is disclosed. The monitor system includes a sensor to produce a signal indicative of a glucose characteristic measured in the user, the sensor further having a sensor port. The monitor system further includes a recorder within a recording housing, the recorder hosing also encompassing a batter. The recorder further includes a recorder port that interfaces with the sensor port in order to receive the produced signals from the sensor port. A recorder clock that assigns a time to the signals from the sensor is also defined within the recorder housing, as is a recorder processor that includes a recorder memory that is coupled to the recorder port to store the produced signals from the sensor. The recorder further includes a data port defined to interface with a dock receiver. A dock that is remotely located from the sensor and the recorder is also included with the monitor system. The dock includes the dock receiver that physically couples the recorder to the dock via the data port and a dock processor that is coupled to the dock receiver. The monitor system further includes a data processor defined to analyze the signals from the sensor that were stored in the recorder. The data processor includes a data processor memory to store data from the recorder and a data processor clock. Further included with the data processor is a program to assign the time and date of the signals from the sensor by comparing the time and date on the data processor clock with the time assigned to the signals from the sensor by the recorder clock.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIGS. 2B-2D illustrate various embodiments of a detail of a recorder port, in accordance with embodiments of the present invention.

FIG. 6A-6C are exemplary schematics illustrating the removal of the recorder from the sensor and placement of the recorder back onto the dock, in accordance with embodiments of the present invention.

DETAILED DESCRIPTION

Figure 1:
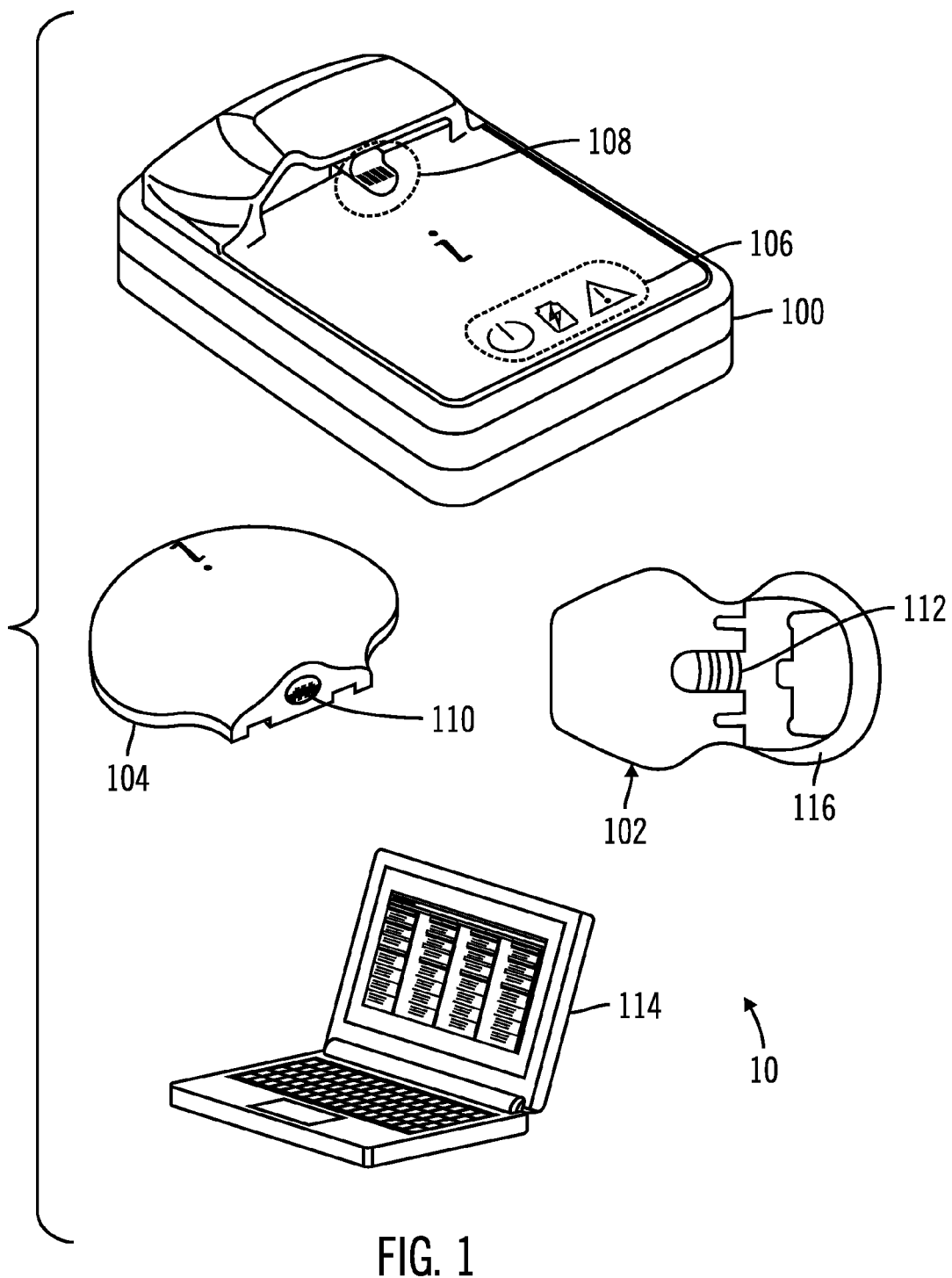
FIG. 1 is an exemplary illustration of components of a monitor system, in accordance with embodiments of the present invention.

As shown in the drawings for purposes of illustration, the invention is embodied in a monitor system coupled to a subcutaneous implantable analyte sensor set to provide continuous data recording of the sensor readings for a period of time. The recorded data later being downloaded or transferred to a computing device to determine body characteristic data based on the data recording over the period of time. In embodiments of the present invention, the analyte sensor set and monitor system are for determining glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the monitor system may also include the capability to be programmed to record data at specified time intervals. The monitor system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, sub-dermal sensors, skin surface sensors, or the like. Embodiments may record sensor readings on an intermittent or continuous basis.

FIG. 1 is an exemplary illustration of components of a monitor system 10, in accordance with embodiments of the present invention. A perspective view of a dock 100 illustrates icon cluster 106 and a dock receiver 108 that is configured to connect to a recorder data port 110 on the recorder 104. The recorder port 110 of the recorder 104 is also configured to connect to a sensor port 112 that is included on a sensor 102. The illustration of the sensor 102 is an exemplary top view of the sensor 102 after it has been inserted into a patient. In some embodiments, the sensor 102 is an assembly commonly known as a "sensor set" that includes, but it not limited to the sensor port 112, sensor adhesive (not shown) covered by an adhesive backing 116, an introducer needle (not shown in FIG. 1), a sensing portion to be placed in a body (not shown), and a mounting base. In many embodiments the sensor set utilizes an electrode-type sensor that is used to monitor blood glucose levels. A data processor 114 is also included in the monitor system 10. In some embodiments the data processor 114 is a general purpose computer such as a netbook, notebook computer or desktop computer that can connect to the dock 100. In other embodiments, the data processor 114 can be more specialized computing devices such as smartphones or purpose built computers. In further embodiments, the data processor includes an Internet connection and employs an Internet-based server and Internet software application.

In some embodiments the recorder 104 is a Holter-type recording device that can be interfaced with both the dock 100 and the sensor 102. In one embodiment the sensor 102 utilizes an electrode-type sensor while in alternative embodiments, the sensor 102 may use other types of sensors, such as chemical based, optical based or the like. In further alternative embodiments, the sensor 102 may be of a type that is used on the external surface of the skin or placed below the skin layer of the user or placed in the blood stream of the user. Other embodiments of a surface mounted sensor would utilize interstitial fluid harvested from the skin.

The recorder 104 generally includes the capability to record and store data as it is received from the sensor 102, and includes a recorder port 110 that can be coupled with either the sensor 102 or the dock 100. When the recorder 104 is coupled to the dock 100 and the dock 100 is in communication with the data processor 114, data stored on the recorder 104 can be transferred to the data processor 114. To enable data transfer between either the sensor 102 or the dock 100 the recorder 104 may include a recorder port 110 that is designed to establish communication between the sensor 102 or the dock 100.

Further description regarding the sensor and associated sensor set can be found in U.S. Pat. No. 6,248,067, entitled ANALYTE SENSOR AND HOLTER-TYPE MONITOR SYSTEM AND METHOD OF USING THE SAME, U.S. Pat. No. 5,586,553, entitled TRANSCUTANEOUS SENSOR INSERTION SET, and U.S. Pat. No. 5,594,643, entitled DISPOSABLE SENSOR INSERTION ASSEMBLY, all of which is herein incorporated by reference.

Figure 2A:
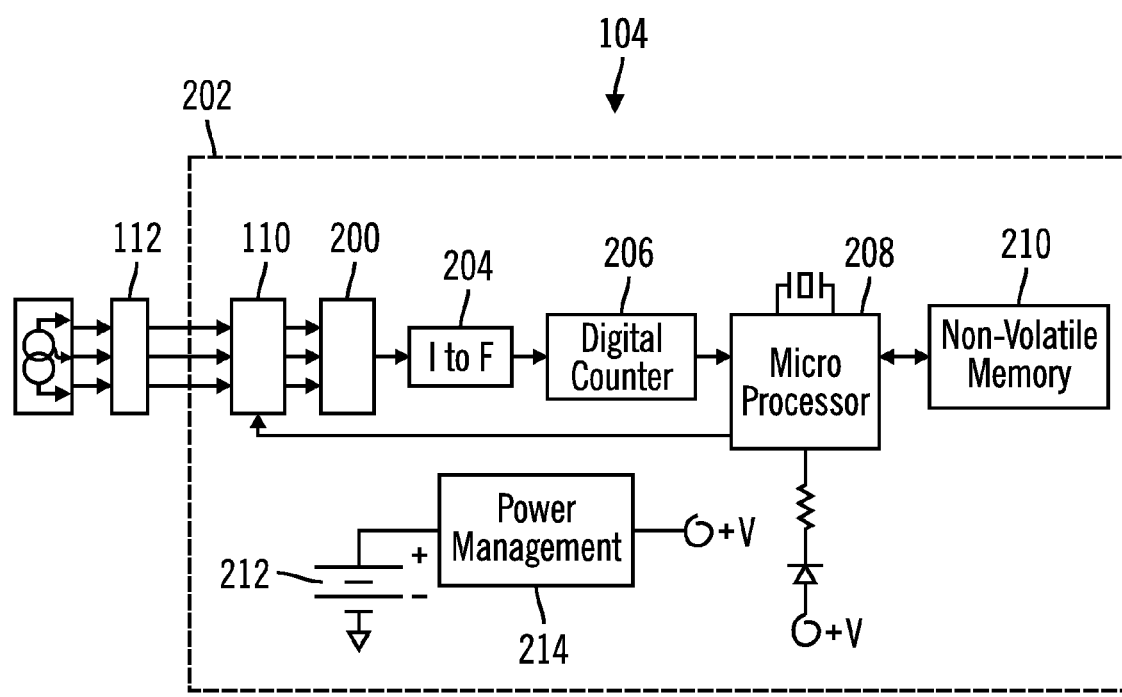
FIG. 2A is an exemplary block diagram illustrating components within a recorder, in accordance with one embodiment of the present invention.

FIG. 2A is an exemplary block diagram illustrating components within the recorder 104, in accordance with one embodiment of the present invention. A power supply 212 connected to power management 214 is found within the housing 202 of the recorder 104. In some embodiments the power supply 212 is a battery assembly that uses a rechargeable battery chemistry to provide power to recorder 104. In one embodiment the power supply 212 is made up of lithium ion battery cells. However, it is understood that alternate battery chemistries may be used, such as nickel metal hydride, alkaline or the like. Similarly, various embodiments can use a single battery cell while other embodiments use multiple battery cells.

The power management 214 includes circuitry and programming to allow recharging of the power supply 212 via the recorder port 110. In some embodiments power management 214 also includes circuitry and programming that enables a low battery warning alarm. In some embodiments the power supply 212 is capable of enabling the recorder 104 to record data for seven days. Additionally, after seven days of recording, the power supply further enables operation of an integrated clock in the recorder 104 for an additional seven days. Alternative embodiments may provide longer or shorter battery lifetimes, or include a power port or solar cells to permit recharging of the power supply 212.

The sensor 102 is connected via the sensor port 112 and the recorder port 110 to a signal conditioning circuit 200, such as a potentiostat or the like, in a housing 202 of the recorder 104. The signal conditioning circuit 200 is in turn connected to a current to frequency converter (I to F) 204. The output of the current to frequency converter 204 is a digital frequency that varies as a function of the sensor signal produced by the sensor 102. In alternative embodiments, other signals, such as voltage, or the like, may be converted to frequency. In one embodiment, the digital frequency is then counted by a digital counter 206, and a value from the digital counter 206 is periodically read and stored with an indication of elapsed time, by a microprocessor 208, into a non-volatile memory 210.

In some embodiments the microprocessor 208 includes an integrated clock that begins tracking elapsed time when the recorder 104 determines the sensor 102 is properly hydrated. The integrated clock is also used to determine when events occur such as periodic sample readings from the sensor 102. The periodic readings from the sensor 102 are stored to the memory 210 with an elapsed clock reading from the integrated clock. In other embodiments, the clock is separate and distinct from the microprocessor 208 but is still contained within the housing 202. In such embodiments, the microprocessor 208 is still programmed and configured to initiate the clock when the sensor 102 is properly hydrated. Additionally, the microprocessor 208 is programmed and configured to read and record the elapsed time of the clock. As will be discussed later, the elapsed clock time from the integrated clock of the recorder 104 can be used to retrospectively determine times of the periodic readings.

In some embodiments, the recorder 104 provides power to drive the sensor 102 via the recorder port 110 and the sensor port 112. Power from the recorder 104 may also be used to speed initialization of the sensor 102, when it is first placed under the skin. The use of an initialization procedure can result in a sensor 102 providing stabilized data in an hour or less compared to requiring several hours before stabilized data is acquired without using an initializing procedure. One exemplary initialization procedure uses a two step process. First, a high voltage (preferably between 1.0-1.2 volts—although other voltages may be used) is applied to the sensor 102 for one to two minutes (although different time periods may be used) to initiate stabilization of the sensor 102. Then, a lower voltage (preferably between 0.5-0.6 volts—although other voltages may be used) is applied for the remainder of the initialization procedure (typically 58 minutes or less). The initialization procedure described above is exemplary and other initialization procedures using differing currents, voltages, currents and voltages, different numbers of steps, or the like, may be used.

FIGS. 2B-2D illustrate various embodiments of detail 220 of the recorder port 110, in accordance with embodiments of the present invention. Detail 220 shows top contacts 222 and bottom contacts 224 which together can simply be referred to as "the recorder contacts". In the embodiment illustrated the recorder contacts are mounted to a circuit board 226 to which the components described in FIG. 2A are also mounted. The recorder contacts can be board mounted springs, or simple contact pads, or any other variety of contact that creates a reliable electrical connection.

The configuration illustrated is intended to be exemplary and should not be construed to be limiting. For example, in alternative embodiments shown in FIG. 2C, rather than a single recorder port 110 (FIG. 2A), the sensor 104 could have two separate ports with the first port 250 providing access to top contacts 222 while the second port 252 provides access to bottom contacts 224. Similarly, other embodiments could use two separate ports while placing the bottom contacts 224 on the same side of the circuit board 226 as the top contacts 222, as shown in FIG. 2D.

As illustrated the recorder contacts are protected from damage and/or fouling by being recessed within the recorder data port 110. In alternative embodiments, the recorder contacts can be exposed on the exterior of the recorder 104 and rely on pins or pads from the both the sensor 102 (FIG. 1) and the dock 100 (FIG. 1) to make electrical contact. The recorder contacts are used for multiple purposes such as, but not limited to, allowing the power supply 212 (FIG. 2A) within the recorder 104 to provide power to the sensor 102 (FIG. 1), transmitting data from the sensor 102 (FIG. 1) to memory 210 within the recorder 104, transmitting data stored in the memory 210 (FIG. 2A) of the recorder 104 to a data processor 114 (FIG. 1), and recharging the power supply 212 (FIG. 2A) of the recorder 104. In some embodiments the top contacts 222 are used to record sensor data and deliver power to the sensor 102. Similarly, the bottom contacts 224 are used to charge the power supply 212 (FIG. 2A), transfer data from the recorder 104 to the data processor 114 and perform diagnostic tests of the recorder components shown in FIG. 2A. The particular examples described above should be considered demonstrative and should not be construed as limiting the present invention. In other embodiments different combinations and configurations of recorder contacts may be used to perform various recorder functions and features.

Figure 3A:
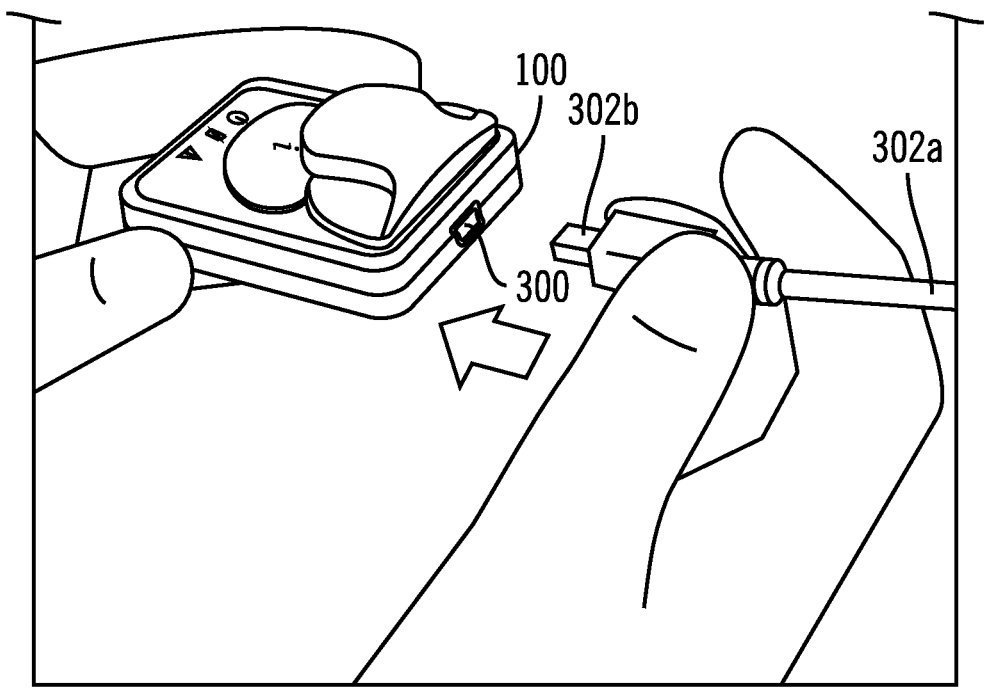
FIGS. 3A-3D are schematic illustrations of connecting a dock to wall plug, in accordance with embodiments of the present invention.
Figure 3B:
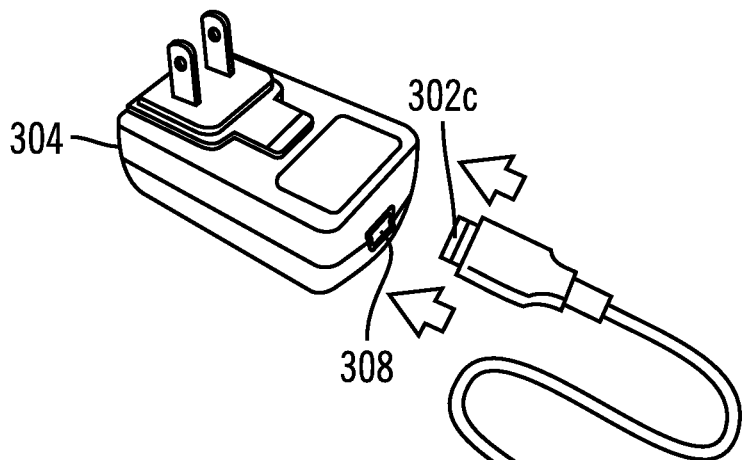
Figure 3B:
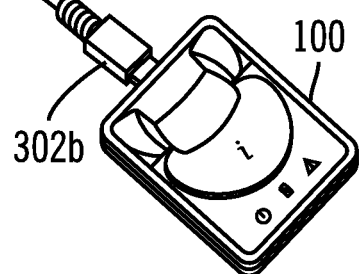

FIGS. 3A-3D are schematic illustrations of connecting the dock 100 to wall plug 304, in accordance with embodiments of the present invention. FIG. 3A illustrates plugging cable 302a into a dock port 300 where the dock port 300 is integrated into the dock 100. In some embodiments the dock port 300 is chosen from a variety of standard ports in order to simplify manufacturing and distribution. As illustrated, the dock port 300 is a standard female mini-USB type connector while cable end 302b is the corresponding standard male mini-USB type connector. Alternate embodiments can use various connectors that are capable of supplying power and transmitting data. For example the cable end 302b could use a proprietary connector and dock port 300 could have a corresponding proprietary socket. Alternatively, a variety of USB connectors and socket could be used, including, but not limited to Type A, Type B, Micro-AB and Micro-B. FIG. 3B illustrates plugging cable end 302c into the wall plug 304. For simplicity of distribution, FIG. 3B shows cable end 302c as Type A USB plug while a plug receptacle 308 is a USB Type A receptacle. As described above, various plugs and receptacles can be used in place of those shown in FIG. 3B.

Figure 3C:
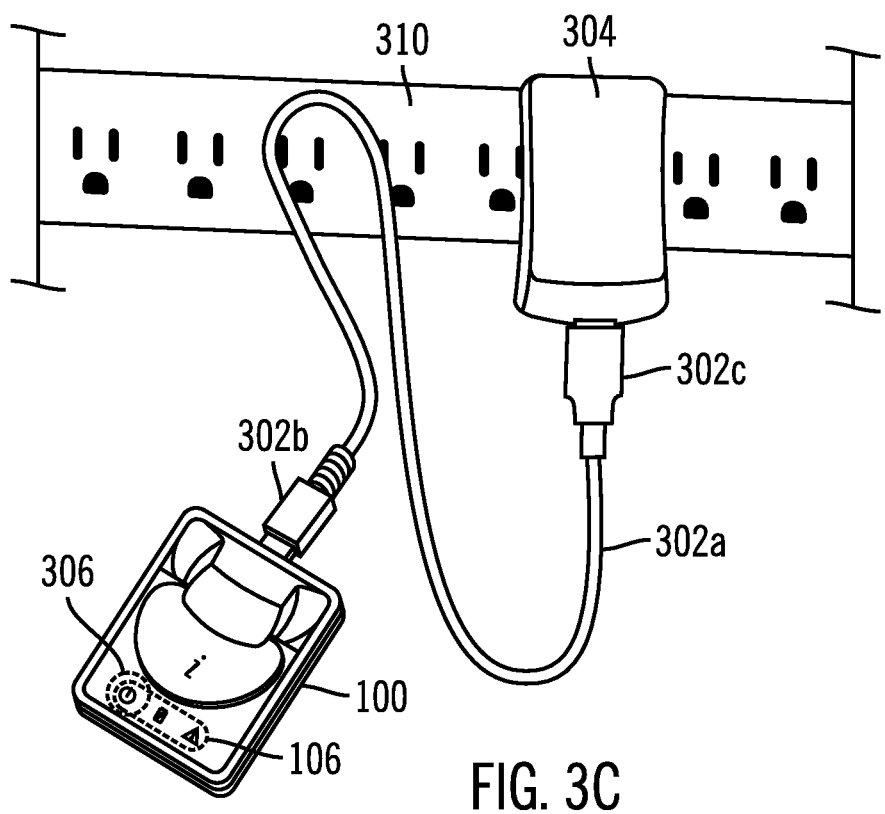

FIG. 3C illustrates a single dock 100 being powered from a power strip 310. The wall plug 304 is connected to the power strip 310 and power is transmitted to the dock 100 via the cable 302a. In one embodiment, the dock 100 includes hardware and software to determine if enough power is being supplied to the dock 100. In situations where the dock 100 is receiving appropriate levels of power the power indicator 306 will be constantly illuminated. The power indicator 306 is part of the icon cluster 106 which will be discussed in more detail during the description of FIGS. 7 and 8.

Figure 3D:
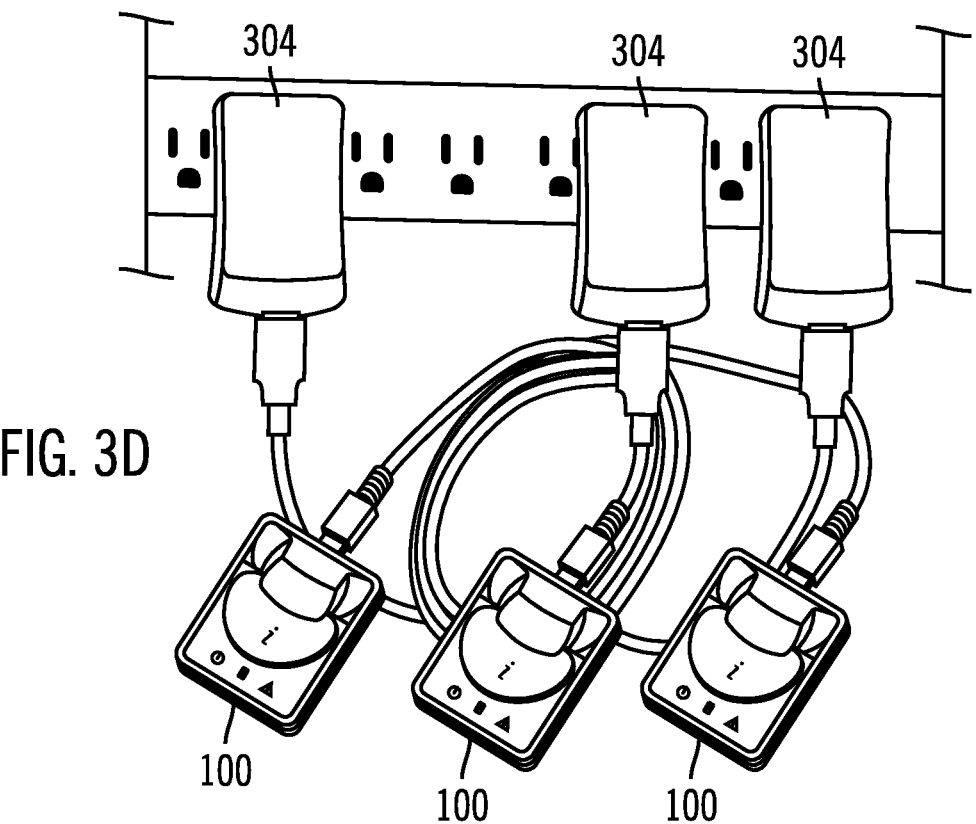

FIG. 3D is an exemplary illustration showing multiple docks 100 each drawing power from the power strip 310 via the wall plugs 304. The ability to supply power to the dock 100 via the wall plug 304 or via a USB port from a data processor 114 (FIG. 1) allows practitioners to use multiple docks 100 without requiring multiple data processors. This allows a practitioner to have a central location for multiple docks 100 separate and distinct from the data processor 114 (FIG. 1). With many practitioners, data processors 114 (FIG. 1) in their office may be located near a reception area that is separated from patient exam or consultation rooms. Thus, depending on placement of data processors in a given office, the ability to charge recorders 104 (FIG. 1) using docks 100 that are simply plugged into a wall may be advantageous as the practitioner may have limited access to data processors 114 (FIG. 1).

Figure 4A:
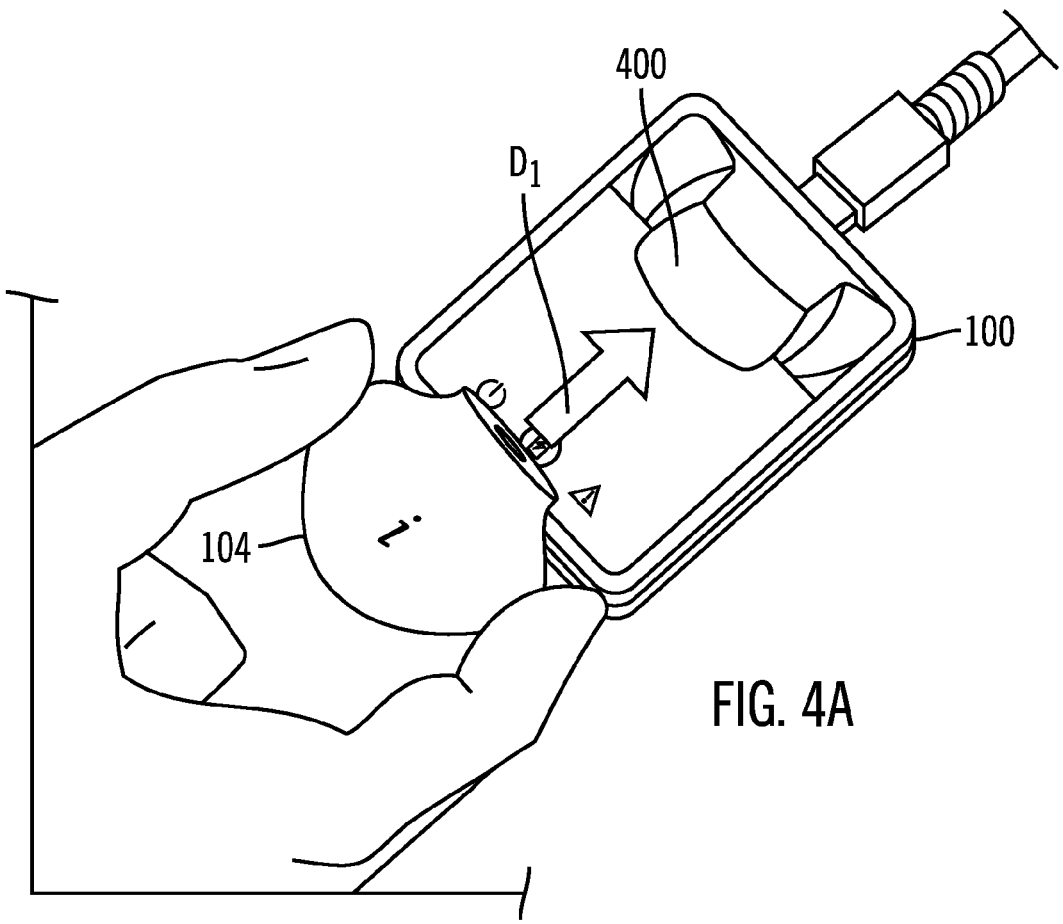
FIGS. 4A and 4B are illustration showing the placement of the recorder onto the dock, in accordance with embodiments of the present invention.
Figure 4B:
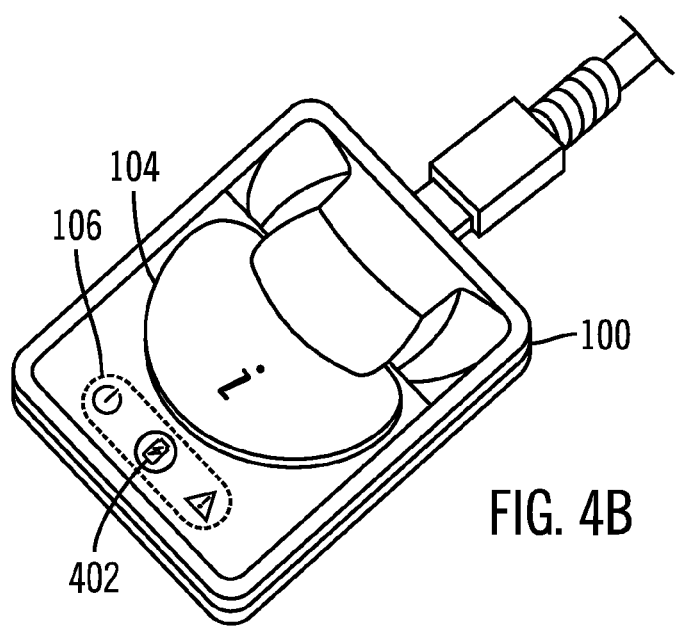

FIGS. 4A and 4B are illustration showing the placement of the sensor 104 onto the dock 100, in accordance with embodiments of the present invention. As shown in FIG. 1, the dock 100 includes dock receiver 108. The dock receiver 108 (FIG. 1) includes electrical contacts that in one embodiment, interface with bottom contacts 224 (FIG. 2B). A hood 400 is included on the dock 100 in order to protect the electrical contacts on the dock receiver 108 (FIG. 1). As shown in FIG. 4A, the hood 400 extends over the dock receiver 108 (FIG. 1) and protects the dock receiver 108 (FIG. 1) from being deformed or rendered unable to couple with the recorder port 110. In the embodiment illustrated in FIG. 4A the recorder 104 is pushed in direction $D_1$ onto the dock receiver 108 (FIG.

1) which results in what is shown in FIG. 4B. Note that the icon cluster 106 remains visible after the recorder 104 is coupled with the dock 100. In some embodiments, an additional cleaning plug (not shown) is used to seal the recorder port 110 to prevent liquids from entering the recorder port 110 so the recorder 104 can be cleaned before the recorder 104 is coupled with the dock 100. The additional step of cleaning the recorder port 110 can reduce or prevent fouling of the dock.

Figure 6D:
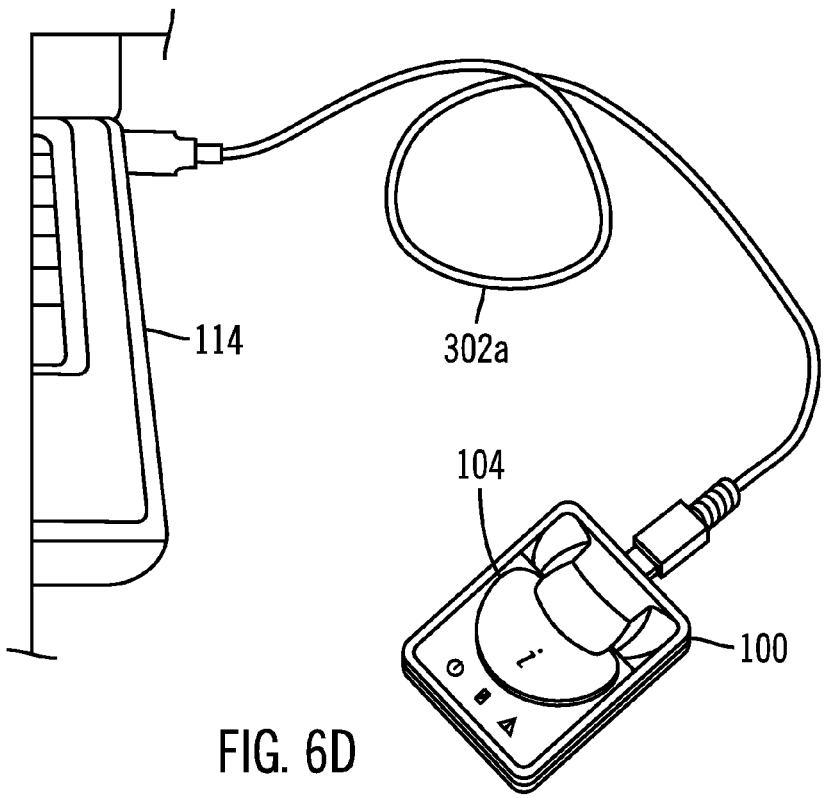
FIG. 6D is an illustration showing a recorder that contains recorded sensor data connected to a dock that is connected to a data processor via a cable, in accordance with embodiments of the present invention.

As previously discussed, the dock 100 can draw power from either a wall plug 304 (FIG. 3C) or data processor 114 (FIG. 1). When the dock 100 of FIG. 4B is connected to sufficient power via a wall plug 304 (FIG. 3C) or via a connection with the data processor 114 as shown in FIG. 6D, hardware and software within the dock 100 will begin charging the power supply 212 (FIG. 2A) within the recorder 104. As will be discussed in the description of FIGS. 7 and 8, a battery indicator 402 on the dock 100 provides actionable user feedback regarding the state of the power supply 212 (FIG. 2A) within the recorder 104.

Figure 5A:
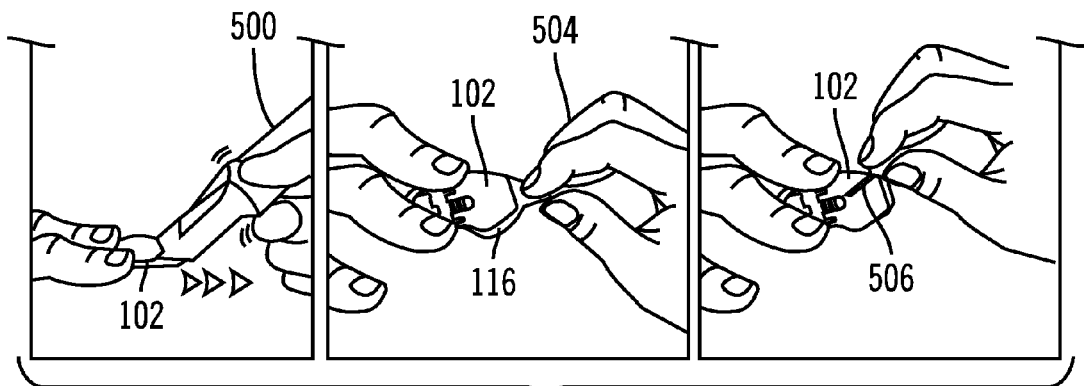
FIGS. 5A-5C are exemplary illustrations of placement of a sensor and installation of the recorder onto the sensor, in accordance with embodiments of the present invention.
Figure 5B:
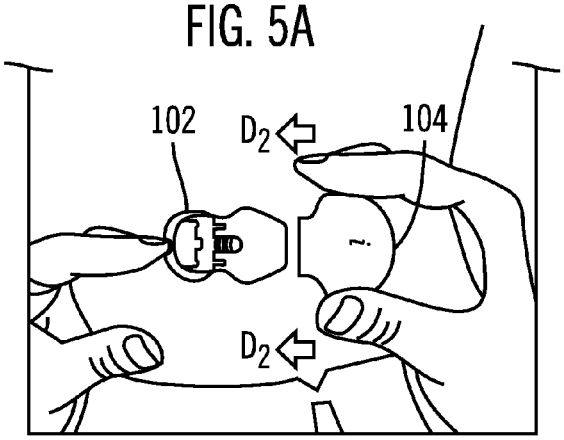
Figure 5C:
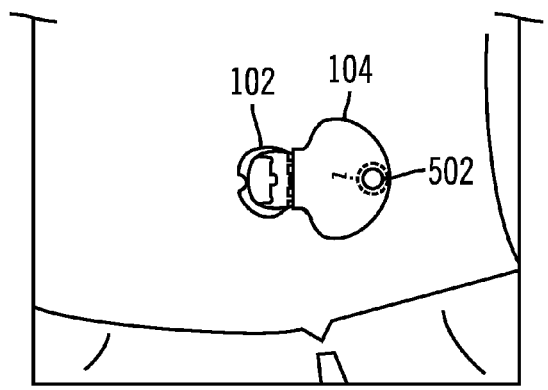

FIGS. 5A-5C are exemplary illustrations of placement of a sensor 102 and installation of the recorder 104 onto the sensor 102, in accordance with embodiments of the present invention. FIG. 5A illustrates a sequence of typical steps used to place the sensor 102 within interstitial fluid of a patient. The leftmost panel of FIG. 5A is illustrative of using an inserter 500 to assist in the installation or placement of the sensor 102. Commonly, inserters 500 are customized to accommodate a specific type of sensor 102. For additional information regarding inserters 500 please see U.S. patent application Ser. No. 10/314,653 filed on Dec. 9, 2002, entitled INSERTION DEVICE FOR INSERTION SET AND METHOD OF USING THE SAME, U.S. Pat. No. 6,607,509, entitled INSERTION DEVICE FOR AN INSERTION SET AND METHOD OF USING THE SAME, and U.S. Pat. No. 5,851,197 entitled INJECTOR FOR A SUBCUTANEOUS INFUSION SET, all of which are herein incorporated by reference.

The middle panel of FIG. 5A is an illustration showing the removal of the adhesive backing 116 to expose an adhesive that enables adhesion of the sensor 102 to the skin 504 of a patient. The rightmost panel of FIG. 5A is an illustration that depicts the removal of an introducer needle 506 that is used during the placement of the sensor 102. FIG. 5B is an exemplary illustration showing the installation of the recorder 104 onto the sensor 102. Direction arrows $D_2$ indicate that the recorder 104 is pushed onto the sensor 102 that was adhered to the patient, as shown in the middle panel of FIG. 5A. In some embodiments, it is desirable to wait a predetermined period of time before installing the recorder 104 onto the sensor 102. For example, it may be advantageous to wait for up to 15 minutes for the sensor 102 to be properly hydrated or wetted by the patient's interstitial fluid before attaching the recorder 104. In other embodiments it may take longer before is sensor is considered properly hydrated. Being able to detect if an installed sensor 102 is properly hydrated can be used by a practitioner to help determine if the sensor was properly installed into the interstitial fluid. In other embodiments there is no minimum time required before attaching the recorder 104 to the sensor 102. In still more embodiments, the sensor 102 need not be hydrated before the recorder 104 is connected. And in additional embodiments, the recorder may be integrated with the sensor before the sensor is inserted into a user.

As illustrated in FIG. 5C, some embodiments of the recorder 104 include a feedback indicator 502. In one embodiment the feedback indicator 502 is a Light Emitting Diode (LED) that can be seen through a translucent or semi-translucent housing. In other embodiments, different light elements can be used, such as, but not limited to incandescent lights, fluorescent lights, Organic Light Emitting Diodes (OLED) or the like. In still other embodiments, the feedback indicator can be an audible tone or a vibration alarm similar to those in mobile phones. In embodiments with the feedback indicator, the recorder 104 can provide feedback regarding the hydration level of a connected sensor. For example, the recorder includes hardware and software that can determine if the sensor 102 is properly hydrated. The feedback indicator 502 can help a practitioner by narrowing the type of troubleshooting that needs to be performed. For example, the feedback indicator 502 can be programmed to flash a specific sequence or color to indicate that the sensor 102 is properly hydrated. Similarly, the feedback indicator 502 can be programmed to flash a different sequence or color to indicate that the sensor is not properly hydrated. In other embodiments, the feedback indicator 502 can further be programmed to flash a particular sequence or color that indicates to a practitioner that the sensor 104 is not fully charged or even that data needs to be transferred from the recorder 104 before additional data can be recorded. The examples provided are not intended to be exhaustive of conditions that can be reported by the feedback indicator 502. The particular examples provided are intended to be exemplary and should not be construed as limiting the scope of the present invention.

In some embodiments, the recorder 104 detects the connection of the sensor 102 and activates the recorder 104 for a specified monitoring period where sensor data is recorded onto the recorder 104, such as 3 days, 4 days, 5 days, 6 days, 7 days, or more. In some embodiments, the recorder 104 will stop recording data after the specified monitoring period. In specific embodiments, the practitioner can program the recorder with a predefined duration that the recorder will operate before it stops collecting sensor data. In particular embodiments the recorder 104 will set an internal "study complete" flag when it stops collecting sensor data and the recorder 104 will not collect more sensor data until the "study complete" flag is removed. In some embodiments the "study complete" flag is removed when the sensor data in the recorder 104 is cleared from the recorder memory, such as by uploading the sensor data to the data processor 114 or by clearing the sensor data without downloading the sensor data first. In particular embodiments, the recorder 104 includes hardware and software to detect when a properly hydrated sensor is connected for the first time and begins to initialize the sensor 102. Additionally, the recorder 104 can set a "study in process" flag, an internal flag such as a bit or switch, so the recorder 104 will not perform an initialization sequence again until after subsequently recorded data is retrieved or downloaded from the recorder 104. Thus, if the sensor 102 is pulled out of the interstitial fluid of a patient, hardware and software within the recorder 104 will detect a change in capacitance measured across two or more sensor electrodes and set a "discard flag" so that all data recorded while the sensor is pulled out and be identified and ignored. Should the sensor be pushed back into the interstitial fluid of the patient, the recorder 104 is able to detect when the sensor 102 is rehydrated by the change in capacitance. Once a rehydrated sensor is detected, the recorder 104 will recognize that the "study in process" flag is set and will not reinitialize the sensor 102. Rather, when a rehydrated sensor is detected, the recorder 104 will remove the discard flag.

In alternative embodiments the recorder 104 will wait a pre-determined period of time for the sensor signal to stabilize before removing the discard flag. The "study in process" flag is removed when the sensor data is cleared from the recorder's memory such as by uploading the data to the data processor 114 or clearing the recorder's memory without uploading data. In some embodiments the pre-determined period of time to wait for sensor signal stabilization is approximately 30 minutes. In other embodiments, additional or less time can be afforded to sensor signal stabilization. Sensor life is improved by not re-initializing the sensor 102 after the sensor is rehydrated and furthermore, power draw from the recorder power supply 212 (FIG. 2A) is minimized. In other embodiments, the recorder 104 can determine if sensor data has been collected, and if sensor data is stored in the recorder's memory, then the recorder 104 will not reinitialize when a rehydrated sensor is detected. The recorder will initialize a sensor only after the sensor data has been cleared from the recorder's memory. For additional information regarding initialization and stabilization of a sensor please see U.S. patent application Ser. No. 12/345,354 filed on Dec. 29, 2008 entitled METHOD AND SYSTEMS FOR OBSERVING SENSOR PARAMETERS which is herein incorporated by reference.

In one embodiment, the recorder 104 is programmed to record periodic sensor data for seven days, as timed by the recorder's internal clock. In one embodiment, the internal clock within the recorder is used to determine the periodic intervals for recording sensor data. Thus, after a predetermined period of time has elapsed after being connected to a hydrated sensor, data from the sensor is recorded with an associated time stamp from the internal clock. For example, if the recorder is programmed to record sensor data every 30 minutes after being connected to a properly hydrated sensor, the first record of sensor data will be time stamped as occurring after 30 minutes. After recording seven days of sensor data the power supply 112 will still have sufficient power to keep the internal clock running for an additional seven to 11 days. In other embodiments, the recorder 104 will supply power for more than 11 days after the sensor data is recorded. The additional seven to 11 days after recording of sensor data has ceased provides enough time for a patient to return to a practitioner's office to return the recorder 104 and give the practitioner time to download or retrieve the stored sensor data from the recorder 104. To retrieve stored sensor data the recorder 104 is placed into a dock 100 that is connected to a data processor 114 (FIG. 1).

FIG. 6A-6C are exemplary schematics illustrating the removal of the recorder 104 from the sensor 102 and placement of the recorder 104 back onto the dock 100, in accordance with embodiments of the present invention. FIGS. 6A and 6B are illustrative of a two step procedure to remove the recorder 104 from the sensor 102. As shown in FIG. 6A a practitioner or the patient squeezes the sensor 102 in the direction $D_3$ in order to release clips or snaps that help connect the recorder 104 to the sensor 102. Subsequently, the recorder 104 is moved in the direction $D_4$ to remove or uncouple the recorder 104 from the sensor 102. After the recorder 104 is removed from the sensor 102, the sensor can be removed from the patient and the recorder 104 can be cleaned using the previously discussed cleaning plug before placing the recorder 104 on a dock 100 as shown in FIG. 6C.

FIG. 6D is an illustration showing a recorder 104 that contains recorded sensor data connected to a dock 100 that is connected to a data processor 114 via cable 302a, in accordance with embodiments of the present invention. A recorder 104 that contains recorded sensor data can be recharged using a dock 100 connected to a wall outlet, however as discussed above, the recorder 104 will have set an internal "study in process" flag that prevents the recorder 104 from performing an additional initialization sequence until the recorded data is retrieved or downloaded from the recorder 104. Thus, it is preferable for recorders 104 with recorded sensor data to be placed on a dock 100 that is connected to a data processor 114. In other embodiments, the recorder 104 will set the "study complete" flag when if the recorder 104 contains sensor data and is connected to the dock 100. Thus, the recorder 104 will collect no additional data until the sensor data in the recorder is cleared, not even if the recorder is reconnected to a hydrated sensor. This helps to minimize the possibility of the recorder 104 containing data from a first patient and then being placed on a second patient before the data is cleared from the first patient. Furthermore, the recorder LED 502 will not flash when connected to a hydrated sensor if the "study complete" flag or the "study in process" flag is set. This tells the practitioner that the recorder 104 is not initializing the sensor.

When the dock 100 is connected to a data processor 114 and the recorder 104 is connected to the dock, 100, stored sensor data can be downloaded from the recorder 104 to the data processor 114. As previously discussed, the stored sensor data includes time stamps regarding when the sensor data was recorded relative to the internal clock of the recorder 104. The time stamped recorded data can be used in conjunction with a clock associated with the data processor 114 to retrospectively determine the actual time data was recorded.

In one embodiment of the present invention, the recorder's internal clock does not stop when the recorder 104 is removed from the sensor 102. Then the recorder 104 is connected to the dock 100 and the dock 100 is connected to the data processor 114 such as by using cable 302a, the recorder can download sensor data to the data processor 114. The recorder 104 provides sensor data that is time stamped with the age of the sensor readings. So, the data processor 114 can refer to a clock associated with the data processor 114 to determine the time and date when the sensor data is downloaded from the recorder 104. Then the data processor 114 can compare the age of the last sensor reading to the time and date when the download occurred to determine the time and date that the sensor data was recorded. This can be done with each sensor reading.

This process of retrospective time stamping can better be appreciated through the following example. In this example when sensor data was downloaded from the recorder 114 to the data processor 114 the clock associated with the data processor indicated 1:00:00 pm on Monday, The downloaded sensor data included the age of each sensor reading. The last sensor reading occurred 4 hours before the sensor data was downloaded to the data processor 114. The data processor 114 subtracts 4 hours from the time and date that the download occurred to determine that the last sensor reading was recorded at 9 AM on Monday morning. The time and date of each sensor reading is calculated similarly.

In an alternative embodiment, the recorder 104 is coupled with a dock 100 that is connected to a data processor 114, the internal clock of the recorder 104 is stopped. In this example, the internal clock of the recorder is stopped at 10 days, 5 hours 15 minutes and 30 seconds. This means the recorder 104 detected a properly hydrated sensor 10 days, 5 hours, 15 minutes and 30 seconds ago. Additionally, 72 hours has elapsed on the internal clock since the last sensor data reading was recorded and the clock of the data processor 114 is reading 3 PM on Apr. 16, 2010. Thus, based on the present time and date reported by the data processor 114 and the elapsed time of the internal clock of the recorder 104, it can be determined that the last sensor reading was taken on Apr. 13, 2010 at 3 PM. As all recorded sensor data includes a time stamp based on the elapsed time of the internal clock, similar retrospective calculations can be used to determine actual time based on the time reported by the data processor 114 for the other recorded sensor data.

In still other embodiments, a Blood Glucose Meter (BGM) or other reference device could be used in conjunction with the sensor and monitor system 10 (FIG. 1) to assist with calibration of sensor data. In one embodiment BGM data is downloaded from the BGM to the data processor 114 and retrospectively time stamped or calibrated similar to the sensor data. Thus, a practitioner will not need to set the proper time and date on the meter before the study. If the time and date of the BGM is incorrect, the data processor 114 can compensate by comparing the time and date of the data processor 114 to the incorrect time of the BMG. The data processor has access to the time and data of the BGM when BGM data is being downloaded from the BGM to the data processor 114. The data processor 114 can apply the difference between the time and date as reported by the BGM and the time and date of the data processor 114 to determine the correct time and date for each BGM reading.

While FIG. 6D and the above description describe data transfer between the recorder 104 and the data processor 114 via the cable 302a, other embodiments allow the dock 100 to draw power through cable 302a while data transfer is conducted using wireless communications such as, but not limited to Wi-Fi, Bluetooth, ultrasonic frequencies, infrared or the like. Additionally, alternate embodiments of the dock 100 do not require the cable 302a to transfer power as the dock can include inductive power capabilities or the dock includes an internal power supply such as a battery.

Figures 7A, 7B, 7C, 7D:
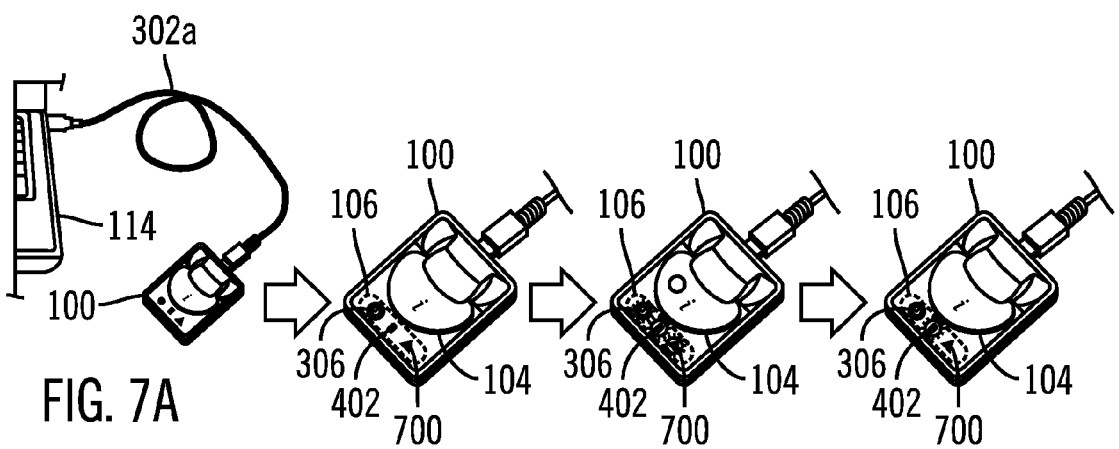
FIGS. 7A-7D are a series of illustrations that demonstrate actionable feedback provided by an icon cluster when the recorder is connected to a dock, in accordance with embodiments of the present invention.

FIGS. 7A-7D are a series of illustrations that demonstrate actionable feedback provided by the icon cluster 106 when the recorder 104 is connected to a dock 100, in accordance with embodiments of the present invention. While the FIG. 7A shows the dock 100 connected to a data processor 114 the dock can include hardware and software that enables the dock 100 to perform the functions described below while being connected to a wall plug 304 (FIG. 3B). FIG. 7B is an exemplary illustration showing the state of icon cluster 106 as the recorder 104 is coupled to the dock 100. Note that power indicator 306 is illustrated as being steadily illuminated while the battery indicator 402 and a warning indicator 700 are not illuminated or flashing. This condition is indicative that the dock 100 is receiving sufficient power from the data processor 114 and the dock 100 has not begun an initialization procedure. In FIG. 7C the recorder 104 has been coupled to the dock 100 and every element within the icon cluster 106, the power indicator 306, the battery indicator 402 and the warning indicator 700 are flashing. This condition indicates that the dock 100 is performing an initialization in response to the recorder 104 being coupled to the dock 100. In one embodiment, if there is sufficient power, the power indicator remains illuminated while the battery indicator and warning indicator are turned off. Using a standard USB cable 302a to supply power to the dock 100 exposes the dock 100 to power inconsistencies from data processor 114 USB ports. Though the USB specification details the power requirement that are required from a USB port, various factors including, but not limited to, cable length, wire gauge within the cable, and the number of devices attached to the bus can affect the actual power supplied to a device.

Notification that the dock 100 is receiving sufficient power is provided to a user by illuminating the power indicator 306, which in one embodiment is a white LED. Thus, when the dock 100 is initialized by either being plugged in or upon detecting the presence of a recorder 104 and the power indicator 306 is not constantly illuminated, it is indicative that the dock 100 is not receiving sufficient power. To rectify the lack of power the user can be instructed to use a powered USB hub, or to try a different USB cable. In embodiments where the dock 100 includes a power indicator and associated hardware and/or software actionable feedback regarding the power supply to the dock 100 can be provided to the user. Without the actionable feedback provided by the power indicator 100 it could be more difficult to troubleshoot issues with both the dock 100 and the recorder 104.

FIG. 7D is an illustration where the power indicator 306 is shown as illuminated while the battery indicator 402 is shown as flashing, in accordance with embodiments of the present invention. A flashing battery indicator 402 can be indicative of two conditions that can occur when the dock 100 is connected to either a wall plug 304 (FIG. 3B) or a data processor 114. A flashing battery indicator 402 provides actionable feedback by indicating that the battery within the recorder 104 is being recharged or that the recorder 104 contains recorded sensor data that has not been downloaded to a data processor 114. When the battery indicator 402 becomes steadily illuminated it is indicative that the battery within the recorder 104 is completely charged. However, if a recorder 104 has stored sensor data the battery indicator 402 will continue to blink even after the battery has been charged. This can notify a practitioner that the recorder 104 needs to be connected to a dock 100 that is connected to a data processor 114 so the stored sensor data can be transferred off of the recorder 104.

As previously discussed, it is only after stored sensor data is transferred or downloaded from the recorder 104 to the data processor 114, that the recorder 104 can be used to record additional sensor data. Thus, it should be apparent to a practitioner that a prolonged flashing battery indicator 402 of a dock 100 may be indicative of a recorder 104 that is not available for use. In one embodiment, the battery indicator is a green LED that can be programmed to flash different sequences to distinguish between a dock 100 that is charging a recorder 104 and a dock 100 that has a recorder 104 containing sensor data. In alternative embodiments, the dock includes an indicator to show the status of the battery within the recorder 104 and a separate indicator to show the status of data stored on the recorder 104.

As mentioned above, the icon cluster 106 also includes a warning indicator 700. This allows the dock 100 to provide actionable feedback regarding the operational readiness of a recorder 104. In addition to providing feedback via the power indicator 306 and the battery indicator 402, the dock 100 includes hardware and software that is able to perform diagnostic testing of a recorder 104 connected to the dock 100. The results of the diagnostic test can be provided as feedback to a user via the warning indicator 700. As previously discussed, the dock 100 includes dock receiver 108 (FIG. 1) that couples with the recorder 104 to recharge the recorder power supply 212, transfer data from the recorder 104, and perform diagnostic tests of electronic components of the recorder 104. As discussed above the recorder 104 includes a memory 210 and a processor 208. In some embodiments, the dock 100 is programmed to perform a diagnostic test of communication between the memory 210 and the processor 208. In other embodiments, the dock 100 performs a test to check the integrity of the memory 210. In still other embodiments, the dock 100 performs tests of the recorder power supply 212. In still other embodiments, the dock 100 verifies that the recorder 104 can communicate with the dock 100 therefore verifying that the recorder's microprocessor 208 is functioning properly and verifying that the connectors 224 in the recorder 104 are not damaged.

While specific types of diagnostic tests have been described above, the types of tests should not be construed as limiting. In other embodiments the dock 100 can be programmed to perform any number of tests only limited by hardware access and programmers inventiveness. A failure of any of the diagnostic tests performed by the dock 100 results in the warning indicator flashing at periodic intervals. Alternatively, the warning indicator can be constantly illuminated if there is a failure of any of the diagnostic tests. In still another embodiment, in order to reduce troubleshooting the warning indicator can flash in specific sequences to indicate which diagnostic test was failed. In particular embodiments, the warning indicator will turn on if the recorder's power supply 212 is too low or is taking too long to charge. In other embodiments, the warning indicator will turn on if the sensor connectors 220 are damaged or if the electronics in the recorder 104 used to operate the sensor are not functioning properly. To convey the seriousness of a failed diagnostic test, in some embodiments the warning indicator 700 is a red LED.

Figure 8A:
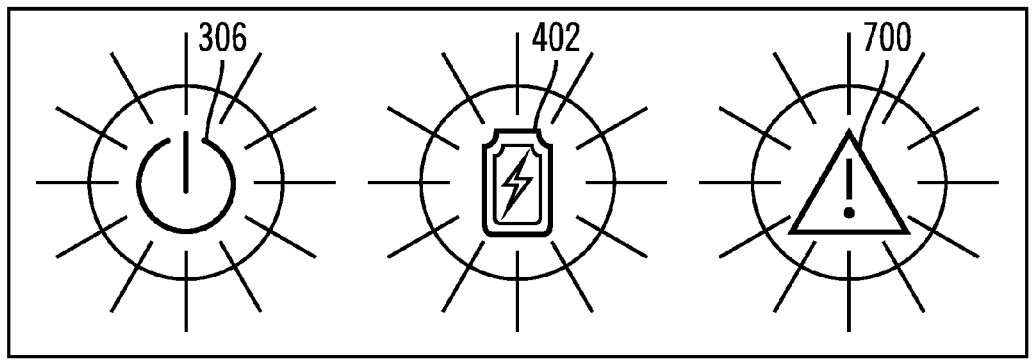
FIGS. 8A-8D are larger illustrations of the icon cluster in accordance with embodiments of the present invention.
Figure 8B:
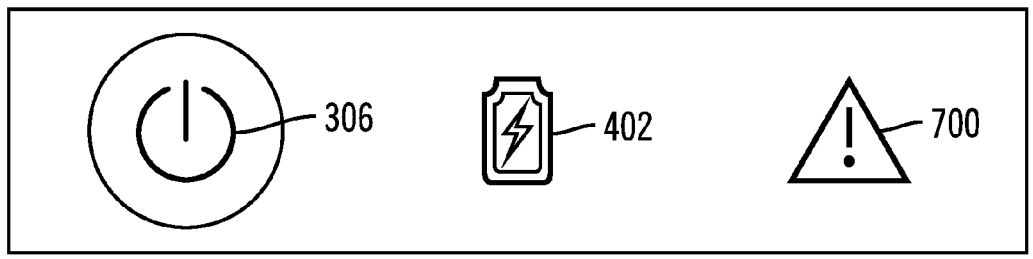
Figure 8C:
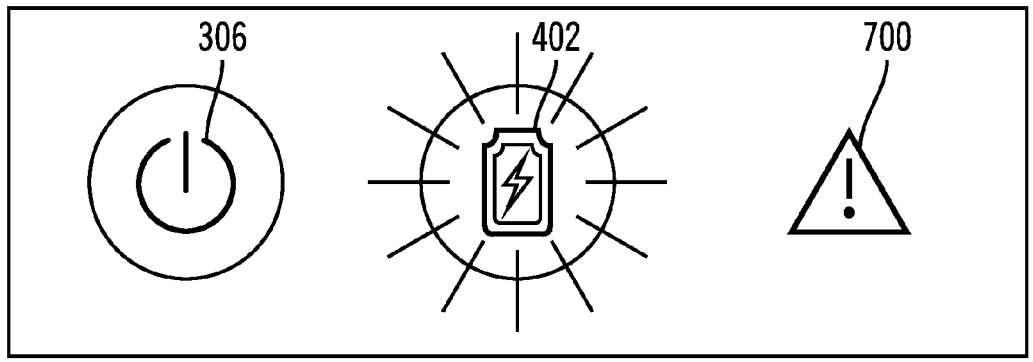
Figure 8D:
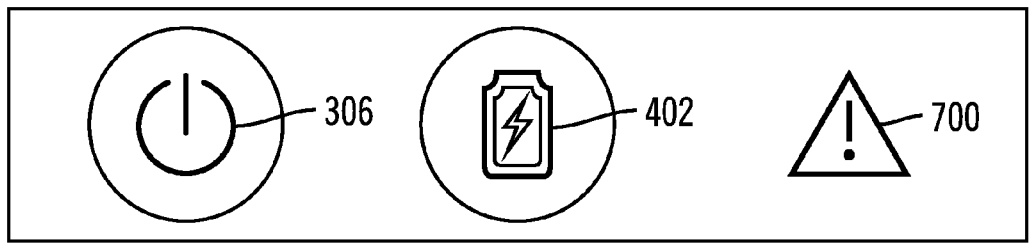

FIGS. 8A-8D are larger illustrations of icon cluster 106 in accordance with embodiments of the present invention. FIG. 8A is an example of the icon cluster 106 where the power indicator 306, the battery indicator 402 and the warning indicator 700 are flashing during initialization of the dock 100. FIG. 8B is an example of the icon cluster 106 when the power indicator 306 is steadily illuminated while the battery indicator 402 and the warning indicator 700 are not illuminated or flashing. This provides feedback to a user by indicating that sufficient power being supplied to the dock 100 and the recorder 104 is not connected to the dock 100. FIG. 8C is an example of the icon cluster 106 when the power indicator 306 is steadily illuminated, the battery indicator 402 is flashing, and the warning indicator 700 is not illuminated nor flashing. This feedback indicates to a user that the dock 100 is receiving sufficient power and either the recorder's power supply 212 is charging or that the recorder 104 contains recorded sensor data that has not been downloaded. FIG. 8D is an example of the icon cluster where the power indicator 306 is steadily illuminated, the battery indicator 402 is steadily illuminated, and the warning indicator 700 is not illuminated nor flashing. Such exemplary feedback is indicative that the recorder 104 in the dock 100 is fully charged and is ready to be connected to a sensor.

The icon cluster is used to provide actionable feedback to a user with the intent of minimizing difficulty when troubleshooting the system while ensuring integrity of data stored on the recorder 104. The use of three different colored LEDs for the power indicator 306, the battery indicator 402 and the warning indicator 700 should not be construed as limiting as a single multicolored LED may be used or combinations of various lighting types. Additionally, the use of only visual feedback should not be construed as limiting. Other embodiments of the dock 100 can include both visual feedback as discussed above along with audible feedback of various frequencies and rhythms.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A monitor system to monitor a characteristic of a user, the system comprising:
   a sensor to produce a sensor signal on a continuous basis, the sensor signal being indicative of a glucose characteristic measured in the user when placed in subcutaneous tissue, the sensor having a sensor port;
   a recorder that includes a recorder housing,
      a battery being contained within the recorder housing,
      a recorder port defined to interface with the sensor port to receive the produced signals from the sensor,
      a recorder clock defined within the recorder housing to assign a time to the signals from the sensor,
      a recorder processor that includes a recorder memory coupled to the recorder port to store the produced signals from the sensor,
   a data port defined to interface with a dock receiver,
   a dock remotely located from the sensor and the recorder, the dock includes the dock receiver to physically couple the recorder to the dock via the data port,
      a dock processor coupled to the dock receiver, and a data processor defined to analyze the signals from the sensor that were stored in the recorder, the data processor includes:
         a data processor memory to store data from the recorder and a data processor clock,
   wherein the data processor is programmed to assign the time and date of the signals from the sensor by comparing the time and date on the data processor clock with the time assigned to the signals from the sensor by the recorder clock,
   wherein the sensor port and the data port are combined into one multifunction port.

2. A monitor system according to claim 1, wherein the data processor is further programmed to convert the signals from the sensor to glucose concentration values experienced by the user.

3. A monitor system according to claim 1, further comprising: a meter having an internal meter clock to provide reference values to the data processor, the reference values including a timestamp from the internal meter clock, and the data processor includes a program to assign time and date to the reference values by comparing the time and date on the processor clock with the timestamp of the reference values from the meter.

4. A monitor system according to claim 1, wherein the dock further includes a dock port.

5. A monitor system according to claim 4, wherein the data processor further includes a data processor port.

6. A monitor system according to claim 5, further comprising a cable defined to interface between the dock port and the data processor port.

7. A monitor system according to claim 1, such that when the recorder is coupled to the dock, the dock is programmed to: (a) recharge the battery of the recorder, (b) perform a diagnostic test of the recorder, and (c) provide actionable feedback based on results of the diagnostic test.

8. A monitor system according to claim 7, wherein the actionable feedback is provided using at least one light integrated into the dock.

9. A monitor system according to claim 7, wherein the actionable feedback is provided using audible tones.

10. A monitor system according to claim 8, wherein a first light condition indicates that the recorder is charging or there are no stored signals from the sensor on the recorder.

11. A monitor system according to claim 7, wherein the diagnostic test includes a test of the recorder processor and the recorder memory.

12. A monitor system according to claim 8, wherein a second light condition indicates a state where the recorder has passed the diagnostic test, the recorder is charged and the recorder contains no stored signals from the sensor.

13. A monitor system according to claim 7, wherein the actionable feedback includes notification when the recorder fails the diagnostic test.

14. A monitor system according to claim 1, wherein the recorder further includes feedback indicator.

15. A monitor system according to claim 14, wherein the feedback indicator is a light that periodically illuminates to indicate proper hydration of the sensor and establishment of communication between the sensor and recorder.

16. A monitor system according to claim 1, wherein the recorder provides power to initialize the sensor.

17. A monitor system according to claim 16, wherein the recorder clock begins running when the sensor is initialized.

18. A monitor system according to claim 17, wherein the recorder automatically stops recording sensor data after the recorder clock has been running for a predefined duration.

19. A monitor system according to claim 18 wherein the recorder clock continues to run after the recorder stops recording sensor data.

* * * * *